(12) United States Patent
Schabbach et al.

(10) Patent No.: US 12,059,554 B2
(45) Date of Patent: Aug. 13, 2024

(54) DRUG DELIVERY DEVICE

(71) Applicant: Sanofi-Aventis Deutschland GMBH, Frankfurt am Main (DE)

(72) Inventors: Michael Schabbach, Frankfurt am Main (DE); Wolfgang Obermeier, Shanghai (CN)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 285 days.

(21) Appl. No.: 16/477,595

(22) PCT Filed: Jan. 18, 2018

(86) PCT No.: PCT/EP2018/051230
§ 371 (c)(1),
(2) Date: Jul. 12, 2019

(87) PCT Pub. No.: WO2018/134316
PCT Pub. Date: Jul. 26, 2018

(65) Prior Publication Data
US 2020/0121856 A1 Apr. 23, 2020

(30) Foreign Application Priority Data

Jan. 20, 2017 (EP) ..................... 17152455

(51) Int. Cl.
*A61M 5/31* (2006.01)
*A61M 5/00* (2006.01)
(Continued)

(52) U.S. Cl.
CPC .......... *A61M 5/3137* (2013.01); *A61M 5/002* (2013.01); *A61M 5/20* (2013.01);
(Continued)

(58) Field of Classification Search
CPC ...... A61M 5/3137; A61M 5/002; A61M 5/20; A61M 5/3202; A61M 2005/3139;
(Continued)

(56) References Cited

U.S. PATENT DOCUMENTS

| 4,217,896 A | 8/1980 | Behnke |
| 6,997,913 B2 | 2/2006 | Wilkinson |

(Continued)

FOREIGN PATENT DOCUMENTS

| CN | 101754778 | 6/2010 |
| CN | 101945679 | 1/2011 |

(Continued)

OTHER PUBLICATIONS

International Preliminary Report on Patentability in International Appln. No. PCT/EP2018/051230, dated Jul. 23, 2019, 8 pages.

(Continued)

*Primary Examiner* — Tasnim Mehjabin Ahmed
(74) *Attorney, Agent, or Firm* — Fish & Richardson P.C.

(57) ABSTRACT

The disclosure relates to a drug delivery device including at least a housing, a drug container with a needle, and a cap, wherein the housing has an inner surface forming a cavity configured to retain the drug container, wherein the cap is configured to be releasably connected to the housing, and wherein a back end of the device opposite to a front end of the device directed to the cap includes a gripping lug axially protruding from the back end of the device. The disclosure further relates to an emergency pack including such a drug delivery device.

19 Claims, 9 Drawing Sheets

(51) Int. Cl.
*A61M 5/20* (2006.01)
*A61M 5/32* (2006.01)
*A61M 5/50* (2006.01)

(52) U.S. Cl.
CPC ... *A61M 5/3202* (2013.01); *A61M 2005/2013* (2013.01); *A61M 2005/3139* (2013.01); *A61M 5/5086* (2013.01); *A61M 2205/583* (2013.01); *A61M 2205/586* (2013.01)

(58) Field of Classification Search
CPC ...... A61M 2205/583; A61M 2205/586; A61M 5/5086; A61M 2005/2013; A61M 5/3204
See application file for complete search history.

(56) References Cited

U.S. PATENT DOCUMENTS

| | | | |
|---|---|---|---|
| 8,412,310 | B2 | 4/2013 | Liu et al. |
| 10,350,357 | B2 | 7/2019 | Park |
| 2004/0039337 | A1 | 2/2004 | Letzing |
| 2009/0182284 | A1* | 7/2009 | Morgan ............... A61M 5/3137 604/198 |
| 2009/0270804 | A1 | 10/2009 | Mesa et al. |
| 2010/0286619 | A1* | 11/2010 | Abry ................... A61M 5/2033 604/192 |
| 2013/0079718 | A1* | 3/2013 | Shang ................. A61M 5/2033 604/131 |
| 2014/0207106 | A1* | 7/2014 | Bechmann .......... A61M 5/2033 604/506 |
| 2014/0296782 | A1* | 10/2014 | Ulrich ..................... A61M 5/31 604/173 |
| 2016/0193414 | A1 | 7/2016 | McLoughlin et al. |
| 2016/0287808 | A1* | 10/2016 | Madsen ................. A61M 5/24 |
| 2016/0303323 | A1 | 10/2016 | Saussaye et al. |
| 2017/0007769 | A1* | 1/2017 | Chang ................. A61M 5/3204 |
| 2017/0007770 | A1* | 1/2017 | Duinat ................. A61M 5/002 |
| 2018/0140781 | A1* | 5/2018 | Kemp ................. A61M 5/3204 |
| 2018/0339112 | A1* | 11/2018 | Wendland ........... A61M 5/3202 |
| 2018/0353702 | A1* | 12/2018 | Jugl .................... A61M 5/3202 |

FOREIGN PATENT DOCUMENTS

| | | |
|---|---|---|
| EP | 3735998 | 11/2020 |
| FR | 2798118 | 3/2001 |
| FR | 2876034 | 4/2006 |
| GB | 2486681 | 6/2012 |
| JP | 2008-522668 | 7/2008 |
| JP | 4926398 | 5/2012 |
| JP | 2013-533096 | 8/2013 |
| JP | 2014-526298 | 10/2014 |
| JP | 2014-532524 | 12/2014 |
| JP | 2015-530199 | 10/2015 |
| JP | 2016-179091 | 10/2016 |
| MX | 2013008440 | 1/2015 |
| WO | WO 2005/115508 | 12/2005 |
| WO | WO 2006/062997 | 6/2006 |
| WO | WO 2009/010591 | 1/2009 |
| WO | WO 2009/090499 | 7/2009 |
| WO | WO 2012/021762 | 2/2012 |
| WO | WO 2013/034984 | 3/2013 |
| WO | WO 2013/070715 | 5/2013 |
| WO | WO 2014/053496 | 4/2014 |
| WO | WO 2015/155482 | 10/2015 |
| WO | WO 2016/102299 | 6/2016 |

OTHER PUBLICATIONS

International Search Report and Written Opinion in International Appln. No. PCT/EP2018/051230, mailed Feb. 26, 2018, 12 pages.

\* cited by examiner

DRUG DELIVERY DEVICE

CROSS REFERENCE TO RELATED APPLICATIONS

The present application is the national stage entry of International Patent Application No. PCT/EP2018/051230, filed on Jan. 18, 2018, and claims priority to Application No. EP 17152455.6, filed on Jan. 20, 2017, the disclosures of which are incorporated herein by reference.

TECHNICAL FIELD

The disclosure generally relates to a drug delivery device. More particularly, the disclosure relates to an emergency pack for use with a drug delivery device.

BACKGROUND

Conventionally, drug delivery devices include a housing or a shell in a shape of a pen which holds a drug cartridge or a drug container or a pre-filled syringe. Some drugs, e.g. emergency drugs like glucagon, are required in small quantities and have special requirements for a fast handling and assistance, in particular for a fast preparation, e.g. opening of the drug delivery device.

Thus, there is a need for an improvement of handling the drug delivery device containing a specific drug, in particular an emergency drug.

SUMMARY

The present disclosure meets the foregoing need by providing a drug delivery device according to claim 1.

Exemplary embodiments are provided in the dependent claims.

In accordance with an aspect of the disclosure, a drug delivery device includes at least a housing, a drug container with a needle and a cap, wherein the housing has an inner surface forming a cavity configured to retain the drug container, wherein the cap being configured to be releasably connected to the housing, in particular at a front end of the device, and wherein a back end of the device opposite to the front end directed to the cap includes a gripping lug axially protruding from the back end of the device.

In an assembled state of the drug delivery device, the housing and the cap are releasably interconnected with each other to encapsulate the drug container.

The device is easy to handle. The gripping lug may include an eyelet or finger loop configured to be gripped by a finger of a user, in particular by index or middle finger. The gripping lug is configured such that a user easily knows how to pull out or open the drug delivery device. Further the gripping lug is configured such that, after a user removed the cap, he still holds the device in the hand. The gripping lug can potentially be used on all kind of drug delivery devices like pre-filled syringes, auto-injectors or pen-injectors.

According to a further embodiment, the gripping lug has an inner surface forming a cavity configured to be assembled onto the back end of the housing. In particular, the cavity includes a form, shape and/or size corresponding to the form, shape and size of the respective back end of the drug delivery device. For instance, the gripping lug is held on to the back end of the housing by at least one of a force-fit connection and form-fit connection.

According to another aspect, the gripping lug includes a retainer configured to be fixed onto the back end of the device, e.g. the housing. In particular, the retainer is formed on the inner surface of the gripping lug. For forming a fixed connection, the retainer includes at least one locking hook radially extending from the inner surface. In a possible embodiment, the retainer includes a plurality of locking hooks all-round protruded and bevelled locking hooks which grab into the outer surface of the housing of the drug delivery device. Hence, the gripping lug may be attached onto different kind of drug delivery devices.

In accordance with a further aspect, the cap has a length which corresponds with the length of the housing. In particular the cap has such a long length that it substantially full covers the drug delivery device, in particular the housing over its entire length including its distal or front end and the needle. Only a proximal end or the back end of the drug delivery device extends from the cap. This proximal end or back end of the drug delivery device is covered by the gripping lug.

In a possible embodiment, the cap and the device, in particular the housing include corresponding crimp interfaces. Alternatively, the cap is releasably coupled to a device, in particular to its housing.

Further, the needle sleeve may include a marker indicating the front end or distal end of the device. In particular, the needle sleeve may include an opening, for instance a triangular opening. The triangular opening points in the direction where the needle will project from the needle sleeve. The needle sleeve may include triangular openings on three sides of the sheath.

Alternatively the needle sleeve may include two or four or more triangular openings.

According to a further aspect, the cap includes a shield grabber connecting the front cap to an outer surface of a needle shield, in particular a so-called rigid needle shield (RNS shield) covering the needle. The needle shield usually made from rubber which seals and covers the needle and the drug container from ambient. Such an integrated shield grabber inside the cap holds the rigid needle shield in an assembled state of the drug delivery device. Thus, removing of the cap will also remove the needle shield from the needle and make the drug delivery device ready to be used. This reduces handling steps for preparation of the drug delivery device.

In particular, the shield grabber is provided with an inner hook element configured and arranged to hook on to an outer surface of the needle shield. In particular, the shield grabber and the needle shield include corresponding crimp features to fixedly hold the shield grabber and the needle shield together, in particular during removing of the cap as well as of the needle shield from the drug delivery device, in particular away from the needle.

The disclosure provides a drug delivery device with a container or a syringe which is prefilled with a drug, in particular an emergency drug, e.g. an allergic drug or a diabetic drug, e.g. hypoglycemia. The drug delivery device is for instance an auto-injector, a pen-injector or a syringe.

In a further embodiment, the drug delivery device includes a piston which slides inside the container to inject the drug. Additionally, the drug delivery device includes actuator means for automatically injecting a patient with said drug.

The disclosure further provides an emergency pack including the above described drug delivery device.

According to a further embodiment, an outer surface of the emergency pack, in particular of the housing or the outer cap, is configured in at least one parameter such that a specific drug contained within the drug delivery device may be quickly and easily identified by a person. In particular, the outer surface of the housing or the outer cap is coloured, e.g. is coloured in orange, red or yellow. Furthermore the outer surface may include a shape or form which allows a fast and easy identification of the specific drug contained within the drug delivery device. For instance, the outer surface may include a pen-shape.

The drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 5 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may be activated via an activation mechanism. Such an activation mechanism can include one or more of a button, a lever, a needle sleeve, or other activation component. Activation may be a one-step or multi-step process. That is, a user may need to activate one or more activation mechanism in order to cause the automated function. For example, a user may depress a needle sleeve against their body in order to cause injection of a medicament. In other devices, a user may be required to depress a button and retract a needle shield in order to cause injection.

In addition, such activation may activate one or more mechanisms. For example, an activation sequence may activate at least two of needle insertion, medicament injection, and needle retraction. Some devices may also require a specific sequence of steps to cause the one or more automated functions to occur. Other devices may operate with sequence independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Further scope of applicability of the present disclosure will become apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE FIGURES

The present disclosure will become more fully understood from the detailed description given below and the accompanying drawings, which are given by way of illustration only, and do not limit the present disclosure, and wherein.

Corresponding parts are marked with the same reference symbols in all figures.

DETAILED DESCRIPTION

Figure 1A:
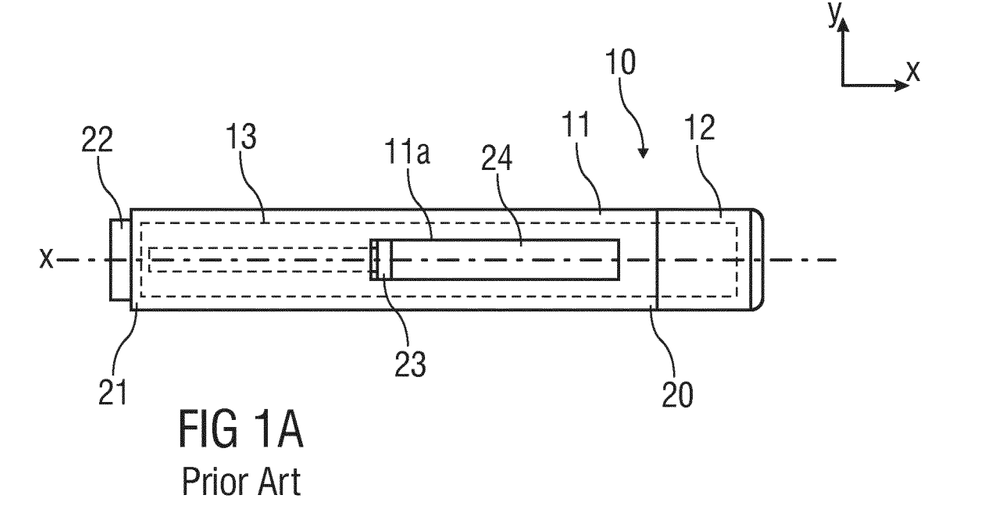
FIGS. 1A to 1C are schematic views of well-known drug delivery devices according to the prior art.
Figure 1B:
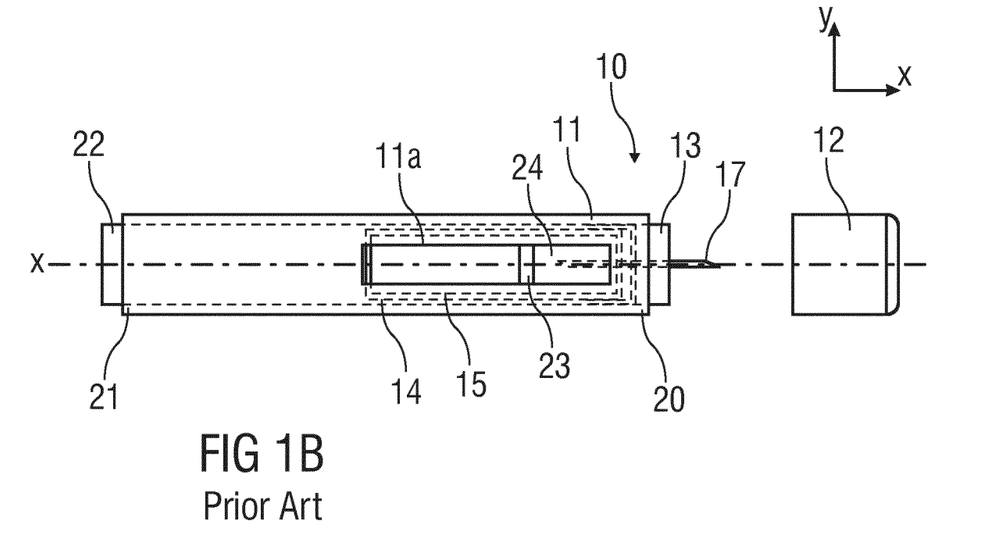

According to some embodiments of the present disclosure, an exemplary drug delivery device 10 is shown in FIGS. 1A and 1B.

Device 10, as described above, is configured to inject a medicament into a patient's body.

Device 10 includes a housing 11 which typically contains a reservoir containing the medicament to be injected (e.g., a syringe or a container) and the components required to facilitate one or more steps of the delivery process.

Device 10 can also include a cap assembly 12 that can be detachably mounted to the housing 11, in particular on a distal or front end D of the device 10. Typically, a user must remove cap assembly or cap 12 from housing 11 before device 10 can be operated.

As shown, housing 11 is substantially cylindrical and has a substantially constant diameter along the longitudinal axis X. The housing 11 has a distal region 20 and a proximal region 21.

The term "distal" refers to a location that is relatively closer to a site of injection, and the term "proximal" refers to a location that is relatively further away from the injection site.

Device 10 can also include a needle sleeve 13 coupled to the housing 11 to permit movement of the sleeve 13 relative to the housing 11. For example, the sleeve 13 can move in a longitudinal direction parallel to longitudinal axis X. Specifically, movement of the sleeve 13 in a proximal direction can permit a needle 17 to extend from distal region 20 of housing 11.

Insertion of the needle 17 can occur via several mechanisms. For example, the needle 17 may be fixedly located relative to housing 11 and initially be located within an extended needle sleeve 13. Proximal movement of the sleeve 13 by placing a distal end of sleeve 13 against a patient's body and moving housing 11 in a distal direction will uncover the distal end of needle 17. Such relative movement allows the distal end of needle 17 to extend into the patient's body. Such insertion is termed "manual" insertion as the needle 17 is manually inserted via the patient's manual movement of the housing 11 relative to the sleeve 13.

Another form of insertion is "automated," whereby the needle 17 moves relative to housing 11. Such insertion can be triggered by movement of sleeve 13 or by another form of activation, such as, for example, a button 22. As shown in FIGS. 1A & 1B, button 22 is located at a proximal or back end P of the housing 11. However, in other embodiments, button 22 could be located on a side of housing 11. In further embodiments, the button 22 has been deleted and is replaced for instance by a sleeve trigger mechanism, e.g. provided by pushing the needle sleeve 13 inside the housing when the drug delivery device is put onto an injection side.

Other manual or automated features can include drug injection or needle retraction, or both. Injection is the process by which a bung or piston 23 is moved from a proximal location within a container or syringe 24 to a more distal location within the syringe 24 in order to force a medicament from the syringe 24 through needle 17.

In some embodiments, a drive spring (not shown) is under compression before device 10 is activated. A proximal end of the drive spring can be fixed within proximal region 21 of housing 11, and a distal end of the drive spring can be configured to apply a compressive force to a proximal surface of piston 23. Following activation, at least part of the energy stored in the drive spring can be applied to the proximal surface of piston 23. This compressive force can act on piston 23 to move it in a distal direction. Such distal movement acts to compress the liquid medicament within the syringe 24, forcing it out of needle 17.

Following injection, the needle 17 can be retracted within sleeve 13 or housing 11. Retraction can occur when sleeve 13 moves distally as a user removes device 10 from a patient's body. This can occur as needle 17 remains fixedly located relative to housing 11. Once a distal end of the sleeve 13 has moved past a distal end of the needle 17, and the needle 17 is covered, the sleeve 13 can be locked. Such locking can include locking any proximal movement of the sleeve 13 relative to the housing 11.

Another form of needle retraction can occur if the needle 17 is moved relative to the housing 11. Such movement can occur if the syringe within the housing 11 is moved in a proximal direction relative to the housing 11. This proximal movement can be achieved by using a retraction spring (not shown), located in the distal region 20. A compressed retraction spring, when activated, can supply sufficient force to the syringe 24 to move it in a proximal direction. Following sufficient retraction, any relative movement between the needle 17 and the housing 11 can be locked with a locking mechanism. In addition, button 22 or other components of device 10 can be locked as required.

In some embodiments, the housing may include a window 11a through which the syringe 24 can be monitored.

Figure 1C:
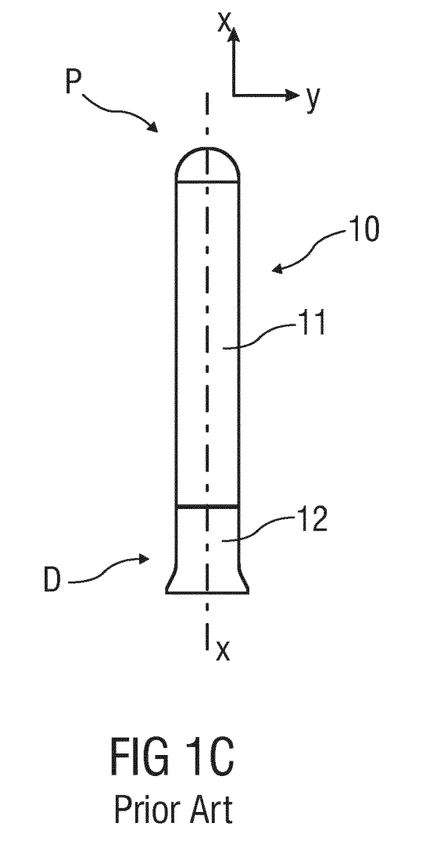

FIG. 1C shows a schematic view of another well-known drug delivery device 10. The drug delivery device 10 includes a cap 12 attached to the housing 11 on a distal end or front end D of the device 10. A back end P of the device 10, in particular of the housing 11 has a curved or dome shape.

The cap 12 has an enlarged distal end. In particular, the cap 12 is substantially cylindrical and has a substantially constant diameter along the longitudinal axis X. At a distal end the diameter of the cap 12 increases and forms an enlarged front end D of the device 10.

Figure 2:
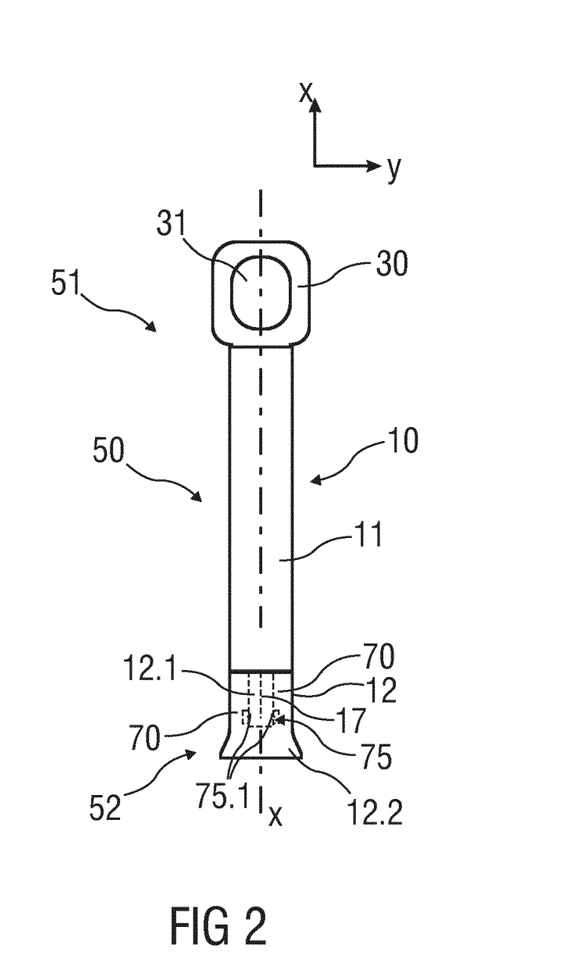
FIG. 2 is a schematic perspective view of an embodiment of a drug delivery device with a gripping lug.

FIG. 2 is a schematic perspective view of an embodiment of a drug delivery device 10 with an integrated gripping lug 30 at a proximal region 21 of the drug delivery device 10.

The drug delivery device 10 is provided with a container 24 which is prefilled with a drug, in particular an emergency drug, e.g. an allergic drug or a diabetic drug, e.g. hypoglycemia or epinephrine. The drug delivery device 10 is for instance an auto-injector, a pen-injector or a syringe. The drug delivery device 10 is finally assembled and a final device which is ready to use.

As shown, the device 10 includes a housing 11 which is substantially cylindrical and has a substantially constant diameter along the longitudinal axis X. Further, the housing 11 includes a round cross section. Alternatively, the housing 11 may include a rectangular, circular or oval cross section.

The drug delivery device 10 with the gripping lug 30 and the cap assembly 12 serves as an emergency medical kit or pack 50. The housing 11 is for instance coloured and labelled according to the emergency medical product. In particular, the housing 11 includes at least an identification portion, e.g. a window, recess, marking or opening. This allows the user to immediately intuitively assess and locate the drug delivery device 10 with the specific emergency medical product without searching devices and medications. The disclosure allows using known and usual drug delivery devices 10, in particular auto-injectors in various styles, for emergency drugs. The housing 11 is configured as strong lightweight outer housing or encapsulation device. In particular, the housing 11 is formed as an outer shell which is closed by the cap assembly 12.

The cap assembly 12 and the gripping lug 30 are tightly closed in an assembled state. In particular, the assembled emergency pack 50 is hermetically sealed or tightly closed.

The gripping lug 30 is configured as one of the easiest mouldable one-part solutions. The gripping lug 30 serves as a de-capping aid, described below in more detail.

The drug delivery device 10, in particular the housing 11 is closed at its distal region 20 by the cap assembly 12 which is formed as a short sleeve. The cap assembly 12 includes an inner needle shield 12.1 and a cap 12.2.

The cap 12.2 includes a shield grabber 75 connecting to an outer surface of the needle shield 12.1 which covers the needle 17. The shield grabber 75 is provided with inner hook element 75.1 configured and arranged to hook on to the outer surface of the needle shield 12.1.

The cap 12.2 is substantially cylindrical and has a substantially constant diameter along the longitudinal axis X. In the distal direction the diameter of the cap 12.2 increases and forms an enlarged distal portion 52 of the pack 50. The cap 12.2 is releasably coupled to the housing 11 at the distal region 20 of the device 10.

A user must remove the cap 12.2 from the housing 11 before the drug delivery device 10 can be operated and used.

The cap 12.2 is for example configured to remove the needle shield 12.1, e.g. a rigid needle shield (RNS shield), from the drug delivery device 10, too. In particular, the cap 12.2 and the needle shield 12.1 are fixedly coupled to each other. Due to coupling of the cap 12.2 with the inner needle shield 12.1, the needle shield 12.1 is simultaneously removable from the drug delivery device 10 while the cap 12.2 is removed from the device 10. After removing of the cap 12.2 together with the needle shield 12.1, the needle 17 of the drug delivery device 10 is further covered by the sleeve 13.

The cap 12.2 and the inner needle shield 12.1 may include corresponding crimp interfaces 70. In particular the crimp interfaces 70 may be formed as a corresponding crimp parts, e.g. a metal crimp and a nut, in particular as a slitted metal crimp engaging a nut. Crimp interfaces 70 allow a holding and fixation of the cap 12.2 together with the inner needle shield 12.1 by its crimp or clamp forces.

Figure 3:
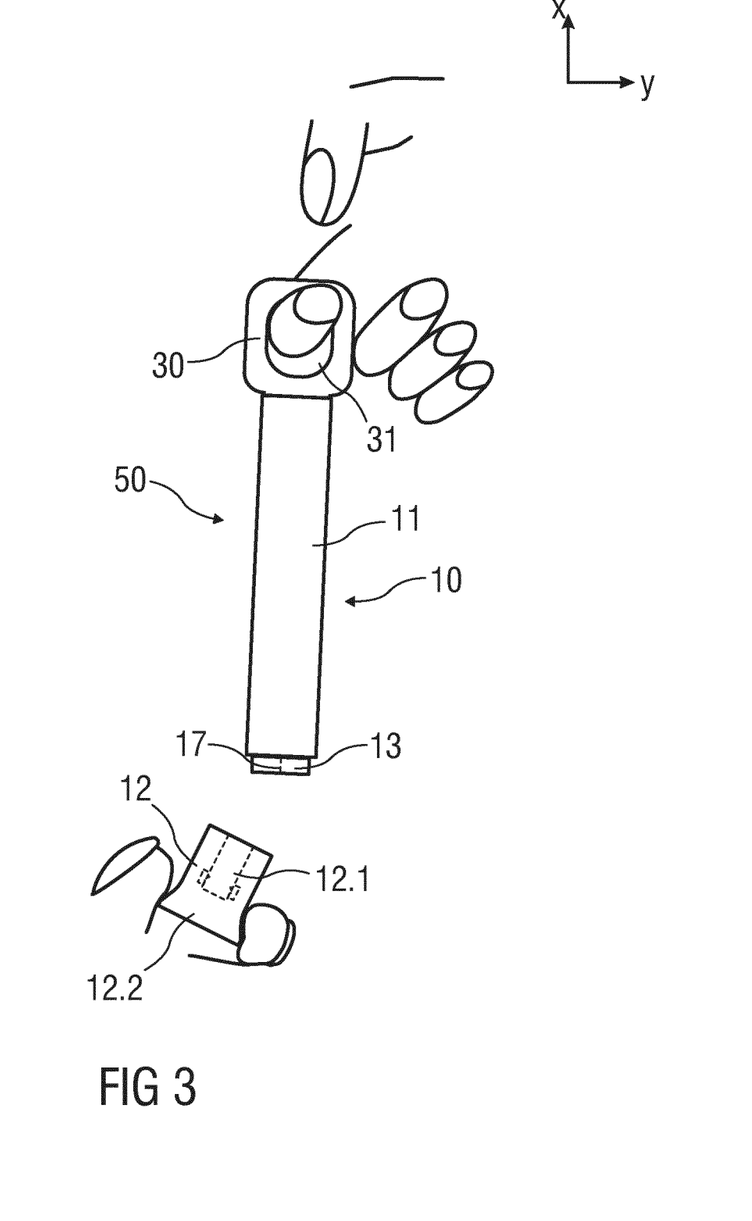
FIG. 3 is an exploded view of a drug delivery device during removing of a cap.

Allowing an intuitive gripping and an easy handling of the device 10, in particular in emergency cases, the gripping lug 30 may include an eyelet 31 or a finger loop. The eyelet 31 is formed for example as a gripping ring or finger loop extending from a proximal portion 51 of the pack 50. The gripping lug 30 is configured so that it could be intuitively gripped by an index finger or a middle finger as it is shown in FIG. 3.

The gripping lug 30 allows an intuitive gripping and, thus, a fast decoupling of the cap 12.2 from the device 10 and, thus, an easy and fast opening of the emergency pack 50 to use the drug delivery device 10 e.g. in an emergency case.

However, in further embodiments, the gripping lug 30 may additionally be configured with a gripping material on the outer surface of the lug 30 and/or as a structured, e.g. profiled outer surface of the lug 30.

Figure 4:
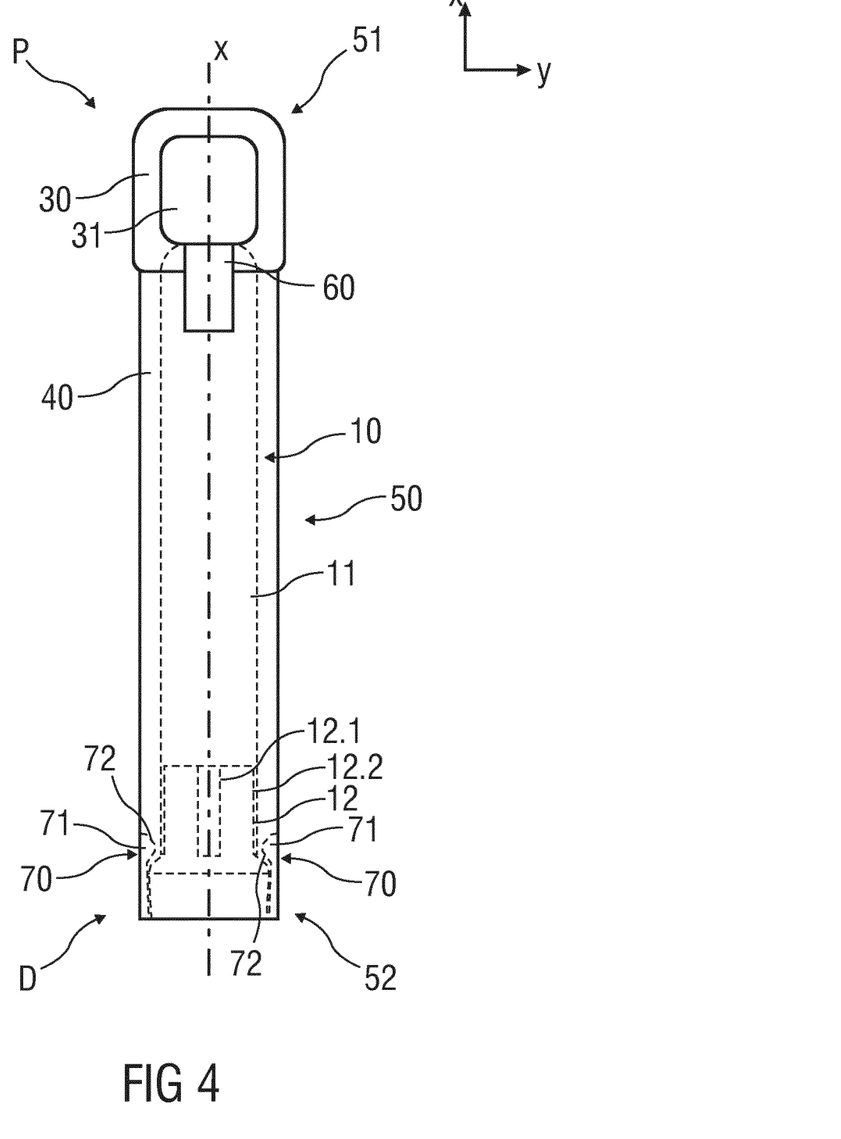
FIG. 4 is a schematic perspective view of a further embodiment of a drug delivery device with a gripping lug.

FIG. 4 is a schematic perspective view of another embodiment of a drug delivery device 10 with a gripping lug 30 and a large outer cap 40.

In particular, FIG. 4 shows an embodiment of an emergency pack 50 including a drug delivery device 10 encapsulated by a gripping lug 30 and an outer cap 40. The outer cap 40 and the gripping lug 30 are configured to form an encapsulation of the drug delivery device 10, in particular in the form of the emergency pack 50.

The drug delivery device 10 is also provided with a container 24 which is prefilled with a drug, in particular an emergency drug, e.g. an allergic drug or a diabetic drug, e.g. Hypoglycemia, as described above.

The drug delivery device 10 is for instance an auto-injector, a pen-injector or a syringe. The drug delivery device 10 is finally assembled and a final device which is ready to use.

As shown, the emergency pack 50 is substantially cylindrical and has a substantially constant diameter along the longitudinal axis X. Further, the emergency pack 50 includes a round cross section. Alternatively, the emergency pack 50 may include a rectangular, circular or oval cross section. The emergency pack 50 has a proximal portion 51 and a distal portion 52.

The emergency pack 50 serves as an emergency medical kit including the drug delivery device 10, with e.g. a prefilled syringe or container 24 in various styles with an emergency medical product or drug, e.g. epinephrine.

The emergency pack 50 is for instance coloured and labelled according to the emergency medical product. In particular, the emergency pack 50 includes at least an identification portion, e.g. a window 11a, recess, marking or opening. This allows the user to immediately intuitively assess and locate the drug delivery device 10 with the specific emergency medical product without searching devices and medications. The disclosure allows using known and usual drug delivery devices 10, in particular auto-injectors in various styles, for emergency drugs.

The emergency pack 50 is configured as strong lightweight outer housing or encapsulation device. In particular, the outer cap 40 is formed as an outer shell which is closed by the gripping lug 30. The outer shell can individually change and is adapted to accommodate the drug delivery device 10 so that no parts of the drug delivery device 10 extend through the emergency pack 50.

The outer cap 40 and the gripping lug 30 are tightly closed in an assembled state. In particular, the assembled emergency pack 50 hermetically seals or tightly closes the drug delivery device 10. Further the emergency pack 50 is reinforced by e.g. reinforcement elements like inner ribs or reinforcement material like reinforced plastic, e.g. fiber-reinforced plastic. The emergency pack 50 is impact-resistant and heat resistant. Hence, the drug delivery device 10 encapsulated by the emergency pack 50 is protected against impacts, heat and/or fluids.

Each component or part, e.g. the outer cap 40 and the gripping lug 30 are conceivable depending on the usability needs. The gripping lug 30 as well as the outer cap 40 is configured as one of the easiest mouldable one-part solutions.

Additionally, a seal element 60, e.g. an O-ring seal or a flexible seal, may be arranged between the outer cap 40 and the gripping lug 30.

The emergency pack 50 is designed to contain at least a drug delivery device 10, e.g. an auto-injector containing a pre-filled syringe or container 24, the outer cap 40 (e.g. a shell) and the gripping lug 30 (e.g. as de-capping aid), described below in more detail.

The drug delivery device 10 is encapsulated by the outer cap 40 which is formed as a long sleeve. The outer cap 40 is substantially cylindrical and has a substantially constant diameter along the longitudinal axis X. The outer cap 40 is releasably coupled to the gripping lug 30 at the back end P of the pack 50 and/or to the housing 11 at its proximal region 21. A user must remove the outer cap 40 from the device 10, in particular from the gripping lug 30 and/or the housing 11 before the drug delivery device 10 can be operated.

The outer cap 40 is for example configured to remove the cap assembly 12, e.g. a rigid needle shield 12.1 (RNS shield) in combination with a cap 12.2 of the drug delivery device 10, too. After removing of the outer cap 40 together with the cap assembly 12 and thus with the cap 12.2 and the rigid needle shield 12.1 from the drug delivery device 10, the needle 17 of the drug delivery device 10 is further covered by the sleeve 13.

De-capping of the emergency pack 50 can occur via several mechanisms. For example, the outer cap 40 may be removed alone from the drug delivery device 10 and the cap assembly 12 may be subsequently removed from the drug delivery device 10. According to another example, due to coupling of the outer cap 40 with the inner cap assembly 12, the cap assembly 12 is simultaneously removable from the drug delivery device 10 while the outer cap 40 is removed from the device 10.

The outer cap 40 and the inner cap assembly 12 may include corresponding crimp interfaces 70. In particular the crimp interfaces 70 may be formed as corresponding crimp parts, e.g. a metal crimp and a nut, in particular as a slitted metal crimp engaging a nut. Crimp interfaces 70 allow a holding and fixation of the outer cap 40 together with the inner cap assembly 12 by its crimp or clamp forces.

In particular, the crimp interfaces 70 include pins or hooks 71 which snap-in into pockets 72 (or windows, recesses, opening) of the cap assembly 12 of the drug delivery device 10. The hooks 71 or pins eliminate free play tolerances between plastic components of the drug delivery device 10 and the emergency pack 50.

Allowing an intuitive gripping and an easy handling of the device 10, in particular in emergency cases, the gripping lug 30 may include the eyelet 31 or a finger loop. The eyelet 31 is formed for example as a gripping ring or finger loop extending from the proximal portion 51 of the pack 50. However, in further embodiments, the gripping lug 30 may additionally be configured as a gripping material on the outer surface of the lug 30 and/or as a structured, e.g. profiled outer surface of the lug 30.

Figure 5:
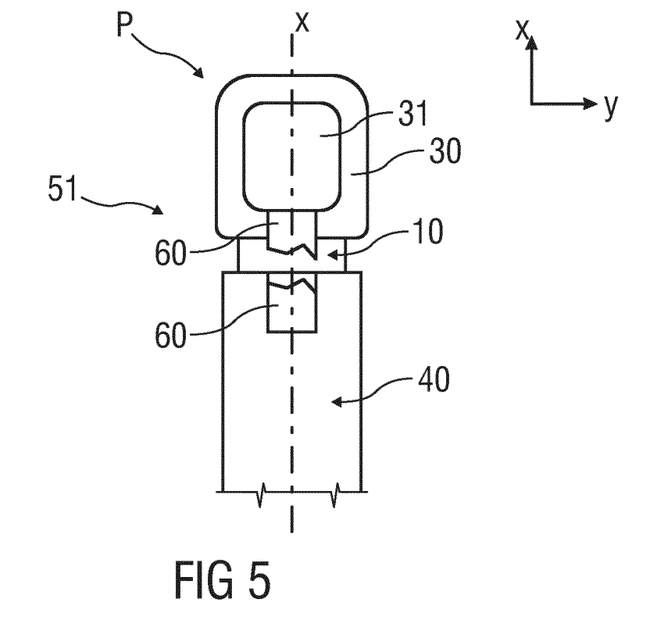
FIG. 5 is an enlarged or sectional view of a drug delivery device with partially removed cap.

The gripping lug 30 allows an easy and fast decoupling of the long outer cap 40 from the device 10 at the proximal portion 51 of the pack 50, in particular in the region of seal element 60. While removing the long outer cap 40 from the drug delivery device 10, in particular from the gripping lug 30 the seal element 60 breaks, as it is shown in FIG. 5.

Figure 6A:
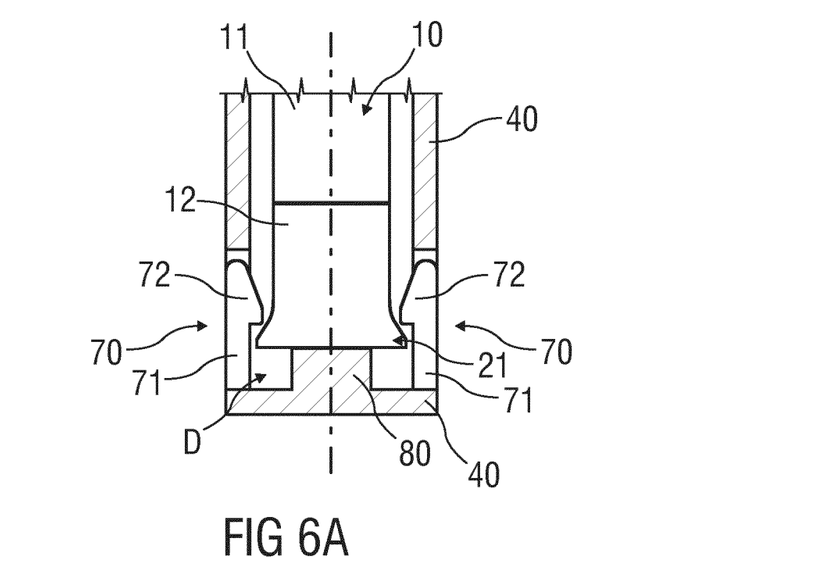
FIG. 6A, 6B is a schematic view of an alternative embodiment for a cap of the drug delivery device.
Figure 6B:
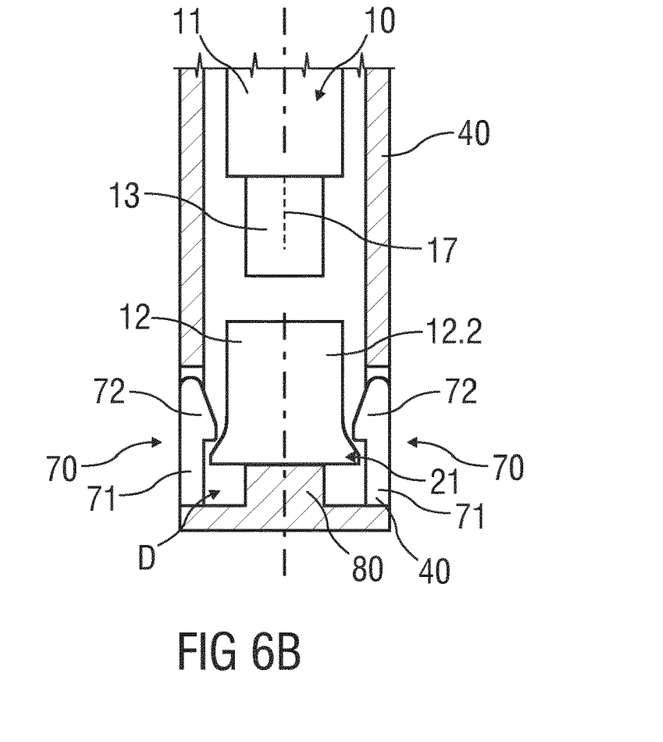

FIGS. 6A, 6B show schematic views of an alternative embodiment for a long outer cap 40 for removing an inner cap assembly 12 from the drug delivery device 10. The long outer cap 40 is coupled to the inner cap assembly 12 of the drug delivery device 10.

The outer cap 40 may include an end stop 80 at its inner distal end. The end stop 80 serves as an interface to the distal region 20 or front end D of the drug delivery device 10, in particular to the distal end of the cap assembly 12 during handling and assembly.

FIG. 6A shows the emergency pack 50 in an assembled state with the cap assembly 12 attached to the drug delivery device 10. FIG. 6B shows the emergency pack 50 in a state in which the outer cap 40 together with the cap assembly 12 is partially removed from the drug delivery device 10. The needle 17 is still covered by the needle sleeve 13.

The crimp interface 70 is configured to fixedly hold the outer cap 40 onto the cap assembly 12. In particular, the crimp interface 70 includes one or more locking arms 71 axially extending from the distal end of the outer cap 40 inwards.

For instance, the arms 71 include fastener 72, e.g. locking hook or snap interface which locks onto the enlarged distal portion of the cap assembly 12 or into a pocket or opening (not shown) of the cap assembly 12. The fasteners 72 are configured to be locked in a friction-fit or force-fit manner.

Figure 7:
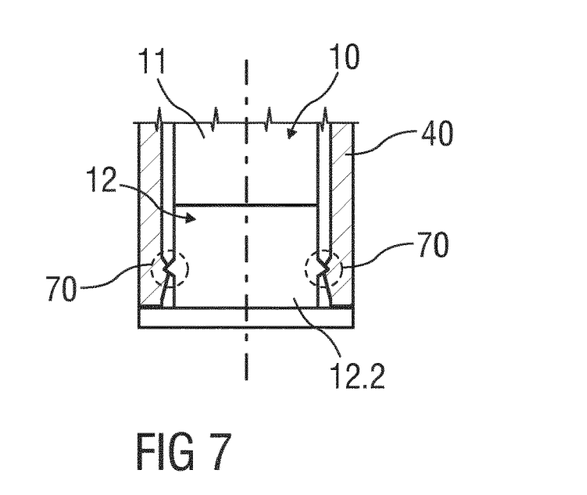
FIG. 7 is an enlarged sectional view of a distal portion of a drug delivery device with an alternative cap assembly.

FIG. 7 shows is an enlarged sectional view of the distal portion 52 of the pack 50 with an alternative integrated crimp interface 70 of the outer cap 40 with the inner cap assembly 12 of the drug delivery device 10. The crimp interface 70 of the outer cap 40 and thus the outer cap 40 are formed as one piece with the inner cap assembly 12. For instance, the outer cap 40 and the inner cap assembly 12 are formed as one-piece part, e.g. as an injection-moulded part.

Figure 8:
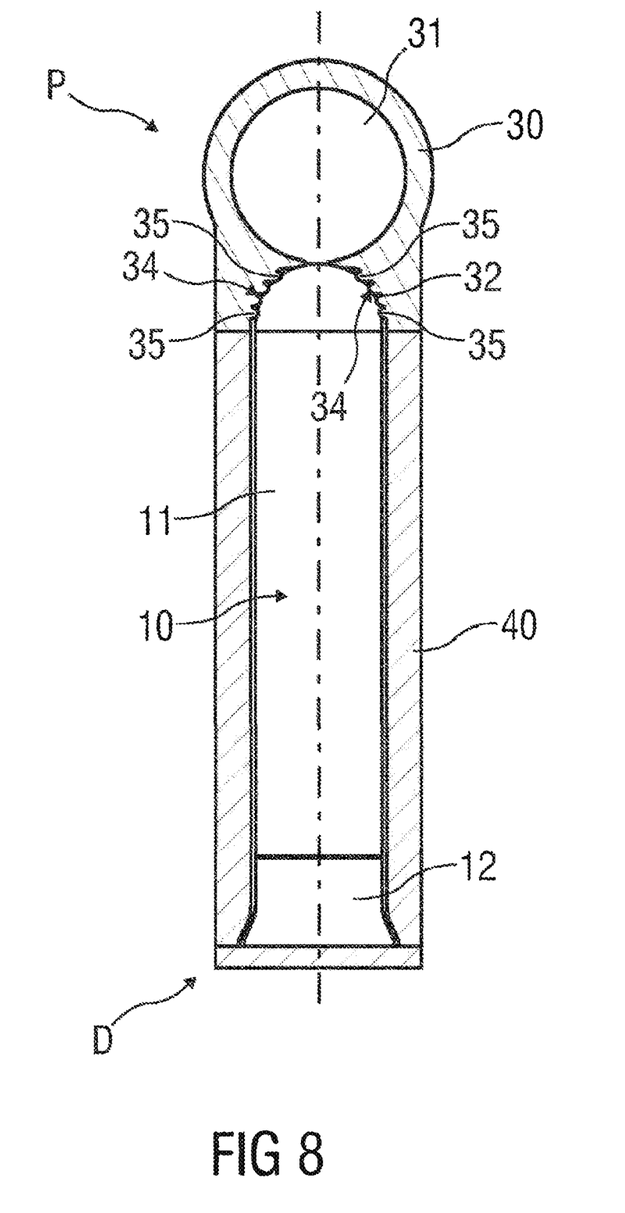
FIG. 8 is a sectional view of an embodiment of a drug delivery device.

FIG. 8 is a sectional view of an embodiment of a drug delivery device 10 with the proximal gripping lug 30. The gripping lug 30 has an inner surface 32 forming a cavity 33 configured to be assembled onto the back end P of the housing 11 of the device 10.

The cavity 33 includes a form, shape and/or size corresponding to the form, shape and size of the respective back end P of the drug delivery device 10. For instance, the back end P of the device 10 has a convex form and the cavity 33 of the lug 30 has a concave form.

Further, the gripping lug 30 is hold on to the back end P of the housing 11 by at least one of a force-fit connection and form-fit connection. For instance, the gripping lug 30 includes an inner retainer 34 configured to be fixed onto the back end P. The retainer 34 is formed on the inner surface 32 of the gripping lug 30. For forming a fixed connection, the retainer 34 includes locking hooks 35 radially extending from the inner surface 32. The locking hooks 35 are bevelled and grab into the outer surface of the housing 11.

FIGS. 9A to 9D are different perspective views showing a removing sequence of a long outer cap 40 from a drug delivery device 10.

Figure 9A:
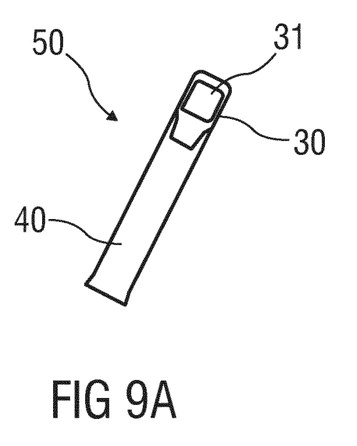
FIGS. 9A to 9D are different perspective views showing a removing sequence of a cap from a drug delivery device.

FIG. 9A shows a delivery state of pack 50 in which the drug delivery device 10 is encapsulated by the outer cap 40 and the gripping lug 30.

Figure 9B:
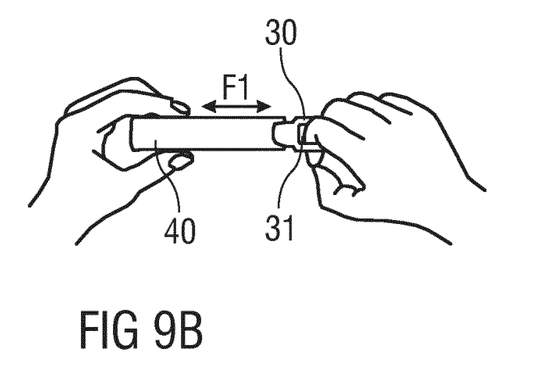

FIG. 9B shows a pre-use state in which a user takes the pack 50 and optionally checks condition of drug and label and grips with his index finger of one hand into the eyelet 31 of the gripping lug 30 and with his outer hand the outer cap 40. Arrow F1 shows how the user can pull the outer cap 40 from the device 10 and the gripping lug 30.

Figure 9C:
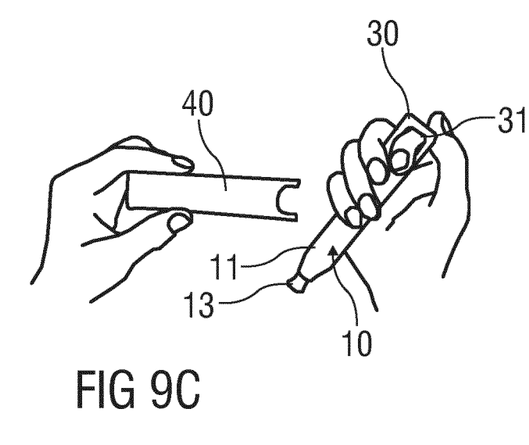

FIG. 9C shows the de-capped pack 50 with the inner drug delivery device 10 which is now ready to use.

Figure 9D:
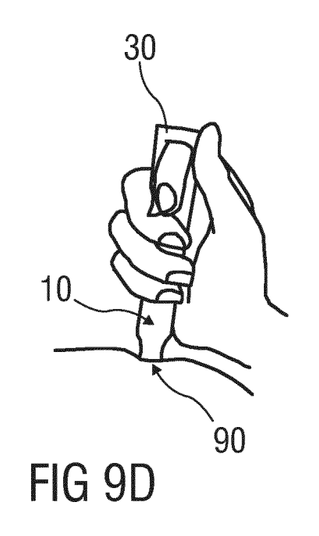

FIG. 9D shows the device 10 in a used state or delivery state in which it is pressed against an injection site 90.

Figure 10A:
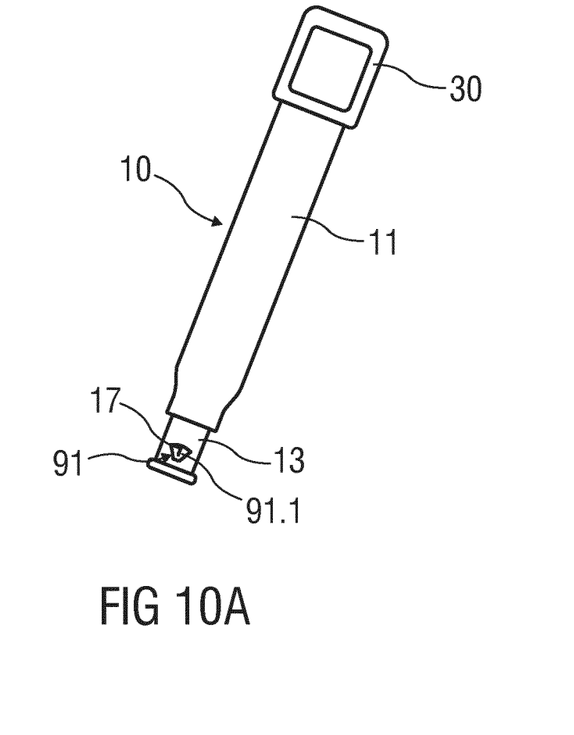
FIGS. 10A, 10B are different perspective views of an alternative embodiment of a drug delivery device with a different cap design.
Figure 10B:
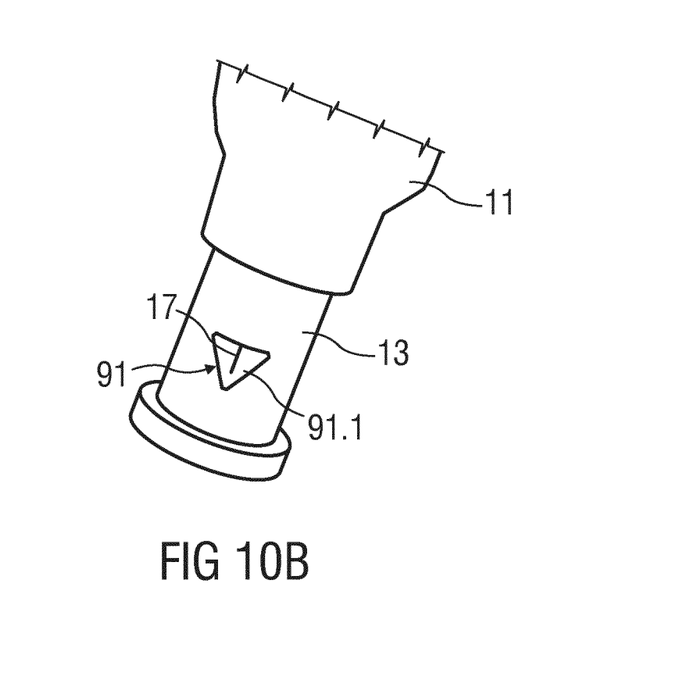

FIGS. 10A, 10B are different perspective views of an alternative embodiment of a drug delivery device 10 with a different cap or needle sleeve design. In particular, the inner needle sleeve 13 of the device 10 includes a marker 91 indicating the front end D or distal end of the device 10. The needle sleeve 13 includes an opening 91.1, for instance a triangular opening. The triangular opening 91.1 points in the direction where the needle 17 projects from the needle sleeve 13.

Additionally, the outer cap 40 may also include such a marker. Other forms, shapes or sizes of markers can be provided for indicating the front end D of the device 10 as well as of the pack 50.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(w-carboxyheptadecanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not include a full-length antibody polypeptide, but that still includes at least a portion of a full-length antibody polypeptide that is capable of binding to an antigen. Antibody fragments can include a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations including (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

LIST OF REFERENCES 10 drug delivery device
11 housing
11a window
12 cap assembly
12.1 needle shield
12.2 cap
13 needle sleeve
17 needle
20 distal region of the drug delivery device
21 proximal region of the drug delivery device
22 button
23 piston
24 syringe or container
30 gripping lug
31 eyelet
32 inner surface
33 cavity
34 retainer
35 locking hooks
40 outer cap
50 emergency pack
51 proximal portion
52 distal portion
60 seal
70 crimp interface
71 arm
72 fastener
75 shield grabber
75.1 hook
80 end stop
90 injection site
91 marker
91.1 opening

The invention claimed is:

1. A drug delivery device comprising:
a housing;
a drug container comprising a needle;
a needle sleeve coupled to the housing and configured to be moveable relative to the housing, the housing being configured to allow the needle sleeve to be pushed into the housing;
an inner cap; and
an outer cap at a front end of the drug delivery device,
wherein the housing has an inner surface forming a cavity configured to retain the drug container,
wherein the outer cap is configured to be releasably connected to the housing,
wherein a back end of the drug delivery device opposite to the front end of the drug delivery device comprises a gripping lug axially protruding from the back end of the drug delivery device,
wherein the gripping lug comprises an eyelet configured to be gripped by a user,
wherein the outer cap has a length such that the outer cap covers at least a majority of an entire length of the housing, wherein the inner cap is arranged within the outer cap and coupled to the outer cap to be released from the housing together with the outer cap, wherein the inner cap comprises an outer diameter which is greater than an inner diameter of the housing at an end of the housing closest to the front end of the drug delivery device and less than an outer diameter of the outer cap.

2. A drug delivery device according to claim 1, wherein the inner surface is a first inner surface and the cavity is a first cavity, and wherein the gripping lug has a second inner surface forming a second cavity configured to be assembled onto the back end.

3. A drug delivery device according to claim 2, wherein the second cavity comprises a form, shape, and/or size respectively corresponding to a form, shape, and/or size of the back end.

4. A drug delivery device according to claim 3, wherein the gripping lug comprises a retainer configured to be fixed onto the back end.

5. A drug delivery device according to claim 4, wherein the retainer is formed on the second inner surface of the gripping lug.

6. A drug delivery device according to claim 5, wherein the retainer comprises a locking hook radially extending from the second inner surface.

7. A drug delivery device according claim 1, wherein the inner cap comprises a crimp interface that corresponds to a crimp interface of a needle shield, or wherein the inner cap comprises a crimp interface that corresponds to a crimp interface of a needle assembly.

8. A drug delivery device according to claim 1, wherein the outer cap is releasably coupled to the drug delivery device.

9. A drug delivery device according to claim 1, wherein the needle sleeve comprises a marker indicating the front end of the drug delivery device.

10. A drug delivery device according to claim 1, wherein the inner cap comprises a shield grabber connecting to an outer surface of a needle shield covering the needle.

11. A drug delivery device according to claim 10, wherein the shield grabber comprises an inner hook element configured and arranged to hook on to an outer surface of the needle shield.

12. A drug delivery device according claim 1, wherein the drug container or a syringe is prefilled with a drug.

13. A drug delivery device according to claim 1, wherein the drug delivery device is an auto-injector, a pen-injector, or a syringe.

14. A drug delivery device according to claim 1, wherein only the back end of the drug delivery device extends from the outer cap.

15. A drug delivery device according to claim 14, wherein the back end of the drug delivery device is covered by the gripping lug.

16. A drug delivery device according to claim 1, wherein a seal element is arranged between the outer cap and the gripping lug, and wherein the seal element is configured to break during removal of the outer cap from the drug delivery device.

17. The drug delivery device according to claim 1, wherein the outer cap substantially fully covers the drug delivery device.

18. The drug delivery device according to claim 1, wherein the gripping lug is fixed onto the back end of the drug delivery device.

19. An emergency pack comprising a drug delivery device, the drug delivery device comprising:
a housing;
a drug container comprising a needle;
a needle sleeve coupled to the housing and configured to be moveable relative to the housing, the housing being configured to allow the needle sleeve to be pushed into the housing;
an inner cap; and
an outer cap at a front end of the drug delivery device,
wherein the housing has an inner surface forming a cavity configured to retain the drug container,
wherein the outer cap is configured to be releasably connected to the housing,
wherein a back end of the drug delivery device opposite to the front end of the drug delivery device comprises a gripping lug axially protruding from the back end of the drug delivery device,
wherein the gripping lug comprises an eyelet configured to be gripped by a user,
wherein the outer cap has a length such that the outer cap covers at least a majority of an entire length of the housing, wherein the inner cap is arranged within the outer cap and coupled to the outer cap to be released from the housing together with the outer cap, wherein the inner cap comprises an outer diameter which is greater than an inner diameter of the housing at an end of the housing closest to the front end of the drug delivery device and less than an outer diameter of the outer cap.

* * * * *

UNITED STATES PATENT AND TRADEMARK OFFICE
CERTIFICATE OF CORRECTION

| | | Page 1 of 1 |
|---|---|---|
| PATENT NO. | : 12,059,554 B2 | |
| APPLICATION NO. | : 16/477595 | |
| DATED | : August 13, 2024 | |
| INVENTOR(S) | : Michael Schabbach and Wolfgang Obermeier | |

It is certified that error appears in the above-identified patent and that said Letters Patent is hereby corrected as shown below:

In the Claims

In Column 15, Line 14, Claim 7, after "according" insert -- to --

In Column 15, Line 32, Claim 12, after "according" insert -- to --

Signed and Sealed this
Twenty-second Day of July, 2025

Coke Morgan Stewart
*Acting Director of the United States Patent and Trademark Office*